(12) United States Patent
De Geus et al.

(10) Patent No.: US 10,750,700 B2
(45) Date of Patent: Aug. 25, 2020

(54) SPROUTING BROCCOLI WITH ONE OR MORE IMPROVED PHENOTYPES

(71) Applicant: Bejo Zaden B.V., Warmenhuizen (NL)

(72) Inventors: Jan De Geus, Oudkarspel (NL);
Johannes Gerardus Maria Hoogland, Hoorn (NL); Albertus Johannes Maria Schrijver, Warmenhuizen (NL)

(73) Assignee: BEJO ZADEN B.V., Warmenhuizen (NL)

( * ) Notice: Subject to any disclaimer, the term of this patent is extended or adjusted under 35 U.S.C. 154(b) by 127 days.

(21) Appl. No.: 15/781,749

(22) PCT Filed: Dec. 8, 2015

(86) PCT No.: PCT/EP2015/079007
§ 371 (c)(1),
(2) Date: Jun. 6, 2018

(87) PCT Pub. No.: WO2017/097345
PCT Pub. Date: Jun. 15, 2017

(65) Prior Publication Data
US 2018/0352777 A1    Dec. 13, 2018

(51) Int. Cl.
*A01H 5/02* (2018.01)
*A01H 6/20* (2018.01)
*A01H 5/10* (2018.01)
*A01H 1/04* (2006.01)

(52) U.S. Cl.
CPC .............. *A01H 6/203* (2018.05); *A01H 1/04* (2013.01); *A01H 5/02* (2013.01); *A01H 5/10* (2013.01)

(58) Field of Classification Search
None
See application file for complete search history.

(56) References Cited

U.S. PATENT DOCUMENTS

2013/0312140 A1    11/2013    Hewitt et al.

FOREIGN PATENT DOCUMENTS

WO    2012083526 A1    6/2012

OTHER PUBLICATIONS

Thompson & Morgan, Broccoli 'Summer Purple' (Purple Sprouting), https://www.thompson-morgan.com/p/broccoli-summer-purple-purple-sprouting/4778TM, 2015.
Shoot Limited, "Brassica oleracea 'Bordeaux' (Broccoli 'Bordeaux')", https://www.shootgardening.co.uk/plant/brassica-oleracea-bordeaux, 2015.
High Mowing Organic Seeds, "Organic Non-GMO Santee", https://www.highmowingseeds.com/organic-non-gmo-santee-fl-sprout-broccoli-a.html , 2015.

*Primary Examiner* — Elizabeth F McElwain
(74) *Attorney, Agent, or Firm* — The Webb Law Firm

(57) ABSTRACT

Provided herein are sprouting broccoli plants, or *Brassica oleracea* convar. *botrytis* var. *asparagoides* plants, with one or more improved phenotypes such as floret development in a single horizontal plane allowing simultaneous harvest of all florets, a reduced cultivation period until harvest and/or not requiring exposure to a cold period below 15° C. during at least one to two weeks. Also provided herein are seeds, cells and plant parts, especially harvestable plant parts such as florets, of the present plants.

13 Claims, 5 Drawing Sheets

1a

1b

2a

2b

3a

3b

4a

4b

4c

4d

5a

5b

5c

5d

SPROUTING BROCCOLI WITH ONE OR MORE IMPROVED PHENOTYPES

CROSS-REFERENCE TO RELATED APPLICATION

This application is the United States national phase of International Application No. PCT/EP2015/079007 filed Dec. 8, 2015, the disclosure of which is hereby incorporated in its entirety by reference.

DESCRIPTION

The present invention relates to sprouting broccoli plants, or *Brassica oleracea* convar. *botrytis* var. *asparagoides* plants, with one or more improved phenotypes such as floret development in a single horizontal plane allowing simultaneous harvest of all florets, a reduced cultivation period until harvest and/or not requiring exposure to a cold period below 15° C. during at least one to two weeks. The present invention further relates to seeds, cells and plant parts, especially harvestable plant parts such as florets, of the present plants.

*Brassica oleracea* is a member of the Brassicaceae family or crucifers (Cruciferae); from this species many cultivars are known; each of them can be considered as showing specialization of a specific part of the plants. For example, with white and red cabbage leaves are prominent, Brussels sprouts are axial buds, cauliflower and broccoli are consumed as juvenile generative tissue.

These cultivars of the *Brassica* family encompass several food crops including—but not limited to—cabbage, broccoli, cauliflower, Brussels sprouts, savoy cabbage, kohlrabi, collards etc.

The wild cabbage is native to Southern and Western Europe; more specific the coastal areas. It is tolerant to saline conditions and these wild species are restricted to said coastal areas. Wild *Brassica oleracea* is a biennial plant, forming a rosette of leaves in the first year. In its second year, after a cold period generally, it produces a flower stalk of approx. 1 to 2 meters bearing a great number of yellow flowers. From this wild species by processes of selection and breeding a range of different cultivars is developed, as described below. Remarkably, (almost) every plant part is as a specialized organ present is one of these cultivars.

Cultivated forms of *Brassica oleracea* are reported from the 6$^{th}$ century and these cultivars spread over Europe in the following centuries.

The most important cultivars of *Brassica oleracea* are:
*B. oleracea* convar. *capitata* var. *alba* (white cabbage, point headed cabbage);
*B. oleracea* convar. *capitata* var. *rubra* (red cabbage);
*B. oleracea* convar. *botrytis* var. *botrytis* (cauliflower, romanesco, broccoli);
*B. oleracea* convar. *botrytis* var. *asparagoides* (sprouting broccoli);
*B. oleracea* convar. *oleracea* var. *gemnifera* (Brussels sprouts);
*B. oleracea* convar. *capitata* var. *sabauda* (savoy cabbage);
*B. oleracea* convar. *acephela* var. *sabellica* (borecole);
*B. oleracea* convar. *acephela* var. *gongyloides* (kohlrabi); and
*B. oleracea* var. *tronchuda* syn. *costata* (Portuguese cabbage, *tronchuda*).

With regard to broccoli and sprouting broccoli, these varieties are known to contain elevated levels of glucosinolates. Many of these compounds are reported to have a potential effect against cancer, with sulforaphane as the prominent example. Furthermore broccoli contains significant amounts of vitamin C, carotenoids, lutein and dietary fiber. The amount of glucosinolates is strongly reduced by prolonged cooking but is retained by rapid stir frying of the product.

Sprouting broccoli, or *Brassica oleracea* convar. *botrytis* var. *asparagoides*, is a specific form of broccoli which does not form a head but is characterized by several single sprouts or florets which can be detached from the plant and serve as a premium vegetable. During harvest many florets can be collected as side shoots after the central floret is harvested.

The term sprouts for the florets of this type of broccoli is well established in the art but must not be confused with the use of the word "sprouts" for young seedlings of several vegetables or Brussels sprouts (young lateral buds of *B. oleracea*) which are also used for consumption.

The crop typically reaches maturity in 115 to 230 days during which also a cold period is necessary to induce development of the—generative—florets or sprouts. During the period between sowing and harvesting, a vernalization of the plants is necessary to induce development of the florets. This vernalization, or induction of flowering, is attained by a cold period of at least one to two weeks with a temperature between 5° C. and 12° C. Once the plant starts producing florets, several secondary side shoots are formed which can be harvested as florets sequentially.

The compulsory vernalization reduces the availability of the product to a relative narrow window during the year. With the material currently available, this compulsory vernalization results in availability of the product a few months after winter (in February/March resp. September/October, depending on the hemisphere) and above all the crop cannot be cultivated in more moderate climate zones as the Mediterranean, subtropical and tropical areas.

Another aspect of this crop is the laborious harvest of the vegetable. The appearance of the crop as it is presently cultivated makes it necessary to detach each sprout individually during harvesting, resulting in that much labour is needed to harvest the crop. Furthermore, harvesting has to be done in several cycles since the sprouts are developing in a range after each other (no uniform size); the last sprouts are harvested about one month after the first ones, on average.

Further, the relatively long period of cultivation, including a cold period, makes the crop more vulnerable to various diseases and disorders.

Considering the above, it is desirable to develop a sprouting broccoli which needs hardly any or no vernalization. Furthermore, it is desirable that sprouts develop after a shorter growing period. This gives the advantage of availability of the product during a longer period, possibly even year-round. Also then the crop can be grown in more subtropical and tropical areas where vernalization is not occurring because of the lack of a cold season.

One major advantage would be the availability of this vegetable in other periods then the restricted timeframe of a few months following winter while another advantage is a reduced exposure to specific diseases and disorders due to the absence of a prolonged cold period.

Considering the above, it is an object of the present invention, amongst other objects, to provide sprouting broccoli plants, or *Brassica oleracea* convar. *botrytis* var. *asparagoides* plants obviating at least partially, if not all, the above problems associated with cultivation of sprouting broccoli.

The above object of the present invention, amongst other objects, is met, according to a first aspect, by providing sprouting broccoli plants as defined in the appended claims.

Specifically, the above object, amongst other objects, is met, according to a first aspect, by the present invention by providing *Brassica oleracea* convar. *botrytis* var. *asparagoides* plants having the phenotype of floret development in a single horizontal plane allowing simultaneous harvest of all florets.

With the purpose to introduce more genetic variation in sprouting broccoli, which goal also encompassed the presence of high levels of glucosinolates in the offspring, a breeding program was performed between broccoli and sprouting broccoli. In this program, a segregating population of plants was obtained wherein surprisingly florets were observed which grew simultaneously in one plane. This is in contrast with the normal habitus of sprouting broccoli plants, where the spears grow laterally on the central stem and develop sequentially. This new and, until now not observed, dominant phenotype gives the unique opportunity to harvest all spears in one step, just by cutting the spears all in one move. The phenotype of floret development in a single horizontal plane allowing simultaneous harvest of all florets can also be designated as the "single cut sprouting broccoli" phenotype.

According to a preferred embodiment, the present invention relates to *Brassica oleracea* convar. *botrytis* var. *asparagoides* plants wherein the plants have the further phenotype of a reduced cultivation period until harvest.

Besides the phenotype "single cut sprouting broccoli", the present plants also surprisingly have a strongly reduced growing or cultivation period. Without being limited to a mechanism underlying this phenotype, the present reduced growth period is likely caused by the absence of the need for vernalization. Therefore typically the growing season has reduced from 115 days minimum to 70 days since a cold period was no longer obliged to induce the development of the florets. The shorter cultivation period also, as an additional advantage, provides plants with a reduced risk of plant diseases and thus a reduced need for agrochemicals resulting in a more sustainable production of the crop.

According to another preferred embodiment of the present invention, the phenotype of a reduced cultivation period until harvest is a dominant phenotype.

According to yet another preferred embodiment of the present invention, the present cultivation period until harvest is reduced by 30% to 50%, such as 35%, 40% or 45%.

According to another preferred embodiment of the present invention, the present plants have a minimal cultivation period until harvest of 50 to 100 days, preferably 60 to 90 days, more preferably 65 to 75 days, such as 55, 65, 70, 80, 85 or 95 days.

According to an especially preferred embodiment of present invention, the present plants have the further phenotype of not requiring exposure of said plant to a cold period below 15° C., or 5° C. to 12° C., during at least one to two weeks and, preferably, the present phenotype of not requiring exposure of said plant to a cold period below 15° C., or 5° C. to 12° C., during at least one to two weeks is a dominant phenotype.

According to a most preferred embodiment, the present invention relates to *Brassica oleracea* convar. *botrytis* var. *asparagoides* plants having the phenotype of floret development in a single horizontal plane allowing simultaneous harvest of all florets and the phenotype of a reduced cultivation period until harvest and the phenotype of not requiring exposure of said plant to a cold period below 15° C., or 5° C. to 12° C., during at least one to two weeks.

The present *Brassica oleracea* convar. *botrytis* var. *asparagoides* plants have the one or more phenotypes as defined above, preferably two, more preferably three, which one or more phenotypes are substantially similar to the respective one or more phenotypes of a *Brassica oleracea* convar. *botrytis* var. *asparagoides* plant deposited under NCIMB 42459.

Preferably, the present *Brassica oleracea* convar. *botrytis* var. *asparagoides* plants have one or more, preferably two, more preferably three, phenotypes obtainable from a *Brassica oleracea* convar. *botrytis* var. *asparagoides* plant deposited under NCIMB 42459.

According to an especially preferred embodiment, the present *Brassica oleracea* convar. *botrytis* var. *asparagoides* plants have one or more, preferably two, more preferably three, phenotypes derived from, or originating from a *Brassica oleracea* convar. *botrytis* var. *asparagoides* plant deposited under NCIMB 42459.

The present *Brassica oleracea* convar. *botrytis* var. *asparagoides* plants are preferably hybrid plants, more preferably sterile hybrid plants, more preferably cytoplasmic male sterile plants.

Most preferably, the present *Brassica oleracea* convar. *botrytis* var. *asparagoides* plant is a plant deposited under NCIMB 42459.

According to another aspect, the present invention relates to seeds, cells or plant parts of a *Brassica oleracea* convar. *botrytis* var. *asparagoides* plant as defined above and according to still another aspect to methods for obtaining a *Brassica oleracea* convar. *botrytis* var. *asparagoides* plant comprising introgressing into a *Brassica oleracea* convar. *botrytis* var. *asparagoides* plant one or more of the phenotypes as defined above.

BRIEF DESCRIPTION OF THE DRAWINGS

The present invention will be further detailed in the following example and figures wherein.

DESCRIPTION OF THE INVENTION

Example 1

Figure 1:
FIG. 1: shows the appearance of "conventional" broccoli showing the dome shaped curd with florets of uneven length (photos 1a and 1b)
Figure 1:
Figure 2:
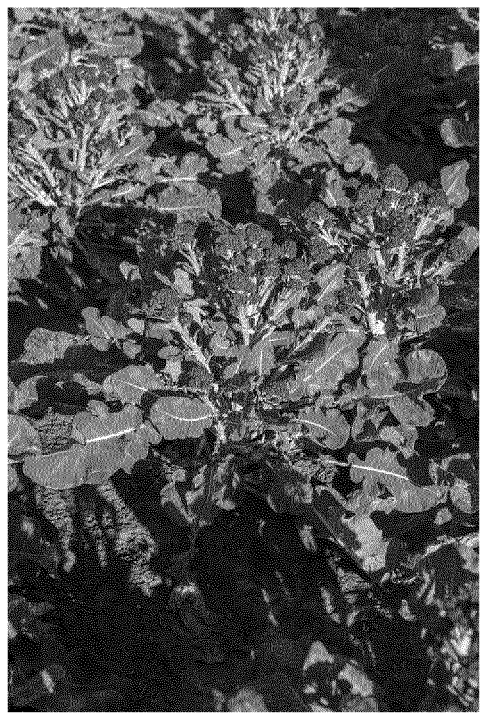
FIG. 2: shows classical sprouting broccoli. Several rounds of harvesting are necessary since development is asynchronous (photos 2a and 2b)
Figure 2:
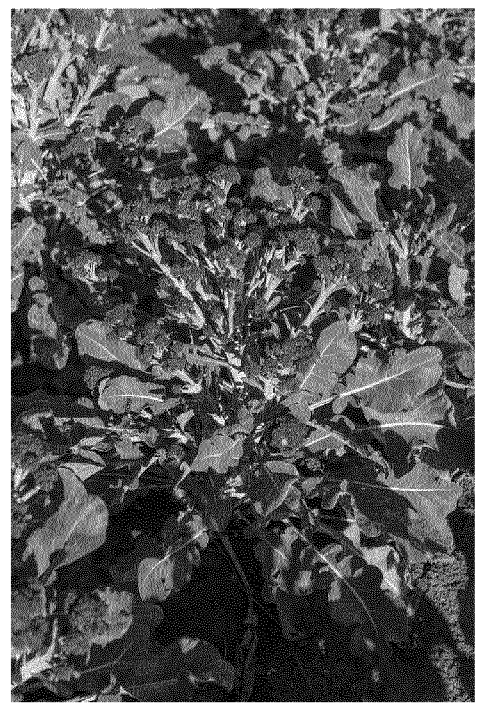
Figure 3:
FIG. 3: shows an illustrative example of the present "one cut" sprouting broccoli with all florets in one plane (photos 3a and 3b)
Figure 3:
Figure 4:
FIG. 4: shows an illustrative example of the plants of photos 3a and 3b which are cut wherein just one cut yields a bunch of florets of similar length (photos 4a to 4d)
Figure 4:
Figure 4:
Figure 4:
Figure 5:
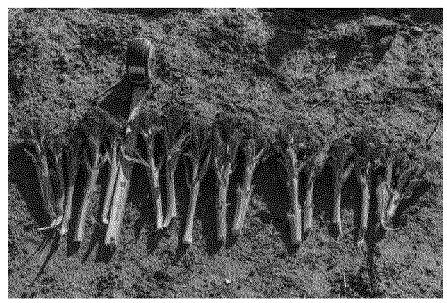
FIG. 5: shows the florets, cut in photos 4b to 4d, arranged to show their equal development (photos 5a to 5d).
Figure 5:
Figure 5:
Figure 5:

In 2003 a cross was made between broccoli (22856) and sprouting broccoli (22101). The hybrid, designated F18065, was self-fertilized and assessed for glucosinolate levels; resulting in plant G12505. This generation was subsequently backcrossed with broccoli 22856, ten plants with purple spears were selected and this population was designated H12147.

Plants from this population were individually self-pollinated and, surprisingly, in this generation the present "single cut" phenotype was observed both with green and purple sprouts in addition to a strongly reduced growing period.

After prolonged selfing from these plants after 4 (purple) to 6 (green) generations genetically stable inbred lines were developed.

From the result of the crosses to develop the selected green resp. purple material it is concluded that inheritance of the described character is not recessive, the breeding program applied is schematically presented here:

| Year | Denomination | Parent 1 | Parent 2 |
|------|--------------|----------|----------|
| 2003 | F18065 | 22856 | 22101 |
| 2004 | G12505 | F18065 inbreeding generation 20 plants selected | |
| 2005 | H12147 | G12505-11 | 22856 |
| 2006 | J11352-1 | H12147 inbreeding generation, green selection | |
| 2006 | J11352-2 | H12147 inbreeding generation, purple selection | |

| Green selection | | | Purple selection | | |
|------|--------------|------|------|--------------|------|
| Year | Denomination | From | Year | Denomination | from |
| 2007 | K5390 | J11352-1 | 2007 | K5408 | J11354-2 |
| 2008 | L6666 | K5390-5 | 2008 | L6686 | K5408-5 |
| 2009 | N7706 | L6666-3 | 2009 | N7739 | L6686-2 |
| 2010 | P6982 | N7706-2 | | | |
| 2011 | R7464 | P6982-2 | | | |
| 2012 | S5716 | R7464-1 | | | |

S5716 = uniform parent line
N7739 = uniform parent line

The developed parent lines are used to produce hybrids. Both a green sprouting broccoli and a purple sprouting broccoli with the "single cut" phenotype and a short growing season are available by crossing appropriate parent lines.

Example 2: Detailed Description of the Purple and Green Sprouting Broccoli

A description of morphological characteristics of a plant according to the invention is presented below.

DEPOSIT INFORMATION

As example, a deposit of *B. oleracea* convar. *botrytis* var. *asparagoides* 954634 is made under the Budapest Treaty at the NCIMB Ltd, Ferguson Building, Craibstone Estate, Bucksburn, Aberdeen AB21 9YA, UK as NCIMB 42459 on Sep. 29, 2015. This example is a green sprouting broccoli hybrid with the described "single cut" phenotype, a short growing season and a lack of necessity of vernalization.

DEFINITIONS

Curd or head: part of a cauliflower or broccoli plant composed of a multitude of inflorescence meristems or juvenile inflorescences. These are arranged in a kind of tree-like structure with an central stalk and several side branches. With cauliflower inflorescences are still meristems which will develop further in inflorescences and eventually form flowers; in broccoli the inflorescences are already developed further but buds are still closed.

Floret: literally small flower but here part of the curd as complete inflorescence, in particular from broccoli Short growing season: a growing period between sowing and harvesting which is reduced from 115 days minimum to 70 days Single cut: a phenotype showing a growth habit of sprouting broccoli wherein all individual florets are of similar size and grow in one plane which enables a simultaneous of harvest all florets Sprout: see floret Sprouting broccoli: refers to *Brassica oleracea* convar. *botrytis* var. *asparagoides* and the sprouts or florets thereof.

Vernalization: the (physiological) process by which a plant acquires the ability to flower by exposure to a prolonged cold period; either by winter or by artificial cold treatment.

The invention claimed is:

1. A *Brassica oleracea* convar. *botrytis* var. *asparagoides* plant having a plurality of florets in a single horizontal plane

| UPOV characteristic accordng to CPVO TP/15/12 | Characteristic | Purple variant | Green variant |
|---|---|---|---|
| 4.1 | Method of maintenance | Hybrid (1) | Hybrid (1) |
| 4.1 | Method of reproduction | Seed propagated (1) | Seed propagated (1) |
| 5.1 | Plant: number of stems | More than one (2) | More than one (2) |
| 5.2 | Plant: height at maturity | Tall (7) | Tall (7) |
| 5.6 | Leaf: number of lobes | Medium (5) | Medium (5) |
| 5.7 | Leaf blade: colour | Blue green (3) | Blue green (3) |
| 5.8 | Leaf blade: intensity of colour | Dark (7) | Dark (7) |
| 5.17 | Head: shape in longitudinal section | Transverse broad elliptic (2) | Transverse broad elliptic (2) |
| 5.18 | Head: colour | Violet (5) | Blue green (4) |
| 5.19 | Head: intensity of colour | Dark (7) | Dark (7) |
| 5.30 | Time of harvest maturity (50% of plants) | Early (3) | Early (3) |
| 5.32 | Male sterility | Present (9) | Absent (1) |
| 7.2.1 | Type of cultivation | Annual (1) | Annual (1) |
| 7.3 | Other information | This variety is a purple sprouting broccoli for harvest period 80 days after transplanting | This variety is a green sprouting broccoli for harvest period 80 days after transplanting | for simultaneous harvest of the plurality of florets, wherein seeds of the plant are deposited under NCIMB 42459.

2. The *Brassica oleracea* convar. *botrytis* var. *asparagoides* plant according to claim 1, wherein the plurality of florets in a single horizontal plane is a dominant phenotype.

3. The *Brassica oleracea* convar. *botrytis* var. *asparagoides* plant according to claim 1, further comprising a phenotype having a cultivation period until harvest of 50 to 100 days.

4. The *Brassica oleracea* convar. *botrytis* var. *asparagoides* plant according to claim 3, wherein the cultivation period until harvest is a dominant phenotype.

5. The *Brassica oleracea* convar. *botrytis* var. *asparagoides* plant according to claim 3, wherein said cultivation period until harvest is 60 to 90 days.

6. The *Brassica oleracea* convar. *botrytis* var. *asparagoides* plant according to claim 3, wherein the cultivation period until harvest is 65 to 75 days.

7. The *Brassica oleracea* convar. *botrytis* var. *asparagoides* plant according to claim 1, further comprising a phenotype that does not require exposure of said plant to a temperature below 15° C. for a period of at least one to two weeks.

8. The *Brassica oleracea* convar. *botrytis* var. *asparagoides* plant according to claim 7, wherein said phenotype of not requiring exposure of said plant to the temperature below 15° C. for a period of at least one to two weeks is a dominant phenotype.

9. The *Brassica oleracea* convar. *botrytis* var. *asparagoides* plant according to claim 1, further comprising a phenotype having a cultivation period until harvest of 50 to 100 days and not requiring exposure of said plant to a cold period below 15° C. for at least one to two weeks.

10. The *Brassica oleracea* convar. *botrytis* var. *asparagoides* plant according to claim 1, wherein said *Brassica oleracea* convar. *botrytis* var. *asparagoides* plant is a hybrid.

11. The *Brassica oleracea* convar. *botrytis* var. *asparagoides* plant according to claim 10, wherein said *Brassica oleracea* convar. *botrytis* var. *asparagoides* plant is a sterile hybrid.

12. Seeds, cells or plant parts of the *Brassica oleracea* convar. *botrytis* var. *asparagoides* plant according to claim 1.

13. The *Brassica oleracea* convar. *botrytis* var. *asparagoides* plant according to claim 11, wherein the plant is a cytoplasmic male sterile hybrid.

* * * * *